(12) United States Patent
Naidu et al.

(10) Patent No.: US 8,940,687 B2
(45) Date of Patent: Jan. 27, 2015

(54) ANTIMICROBIAL ANGIOGENIN COMPLEXES (ANGEX) AND USES THEREOF

(71) Applicant: Naidu LP, Pomona, CA (US)

(72) Inventors: A. Satyanarayan Naidu, Diamond Bar, CA (US); A. G. Tezus Naidu, Santa Ana, CA (US); A. G. Sreus Naidu, Santa Ana, CA (US)

(73) Assignee: Naidu LP, Pomona, CA (US)

( * ) Notice: Subject to any disclaimer, the term of this patent is extended or adjusted under 35 U.S.C. 154(b) by 0 days.

(21) Appl. No.: 13/861,236

(22) Filed: Apr. 11, 2013

(65) Prior Publication Data

US 2013/0287754 A1    Oct. 31, 2013

Related U.S. Application Data

(60) Continuation of application No. 13/185,115, filed on Jul. 18, 2011, now Pat. No. 8,440,183, which is a division of application No. 12/554,602, filed on Sep. 4, 2009, now Pat. No. 8,003,603, which is a division of application No. 11/734,729, filed on Apr. 12, 2007, now Pat. No. 7,601,689.

(51) Int. Cl.

| *A61K 38/54* | (2006.01) |
|---|---|
| *C07K 14/515* | (2006.01) |
| *A61K 38/43* | (2006.01) |
| *A61K 39/395* | (2006.01) |
| *G01N 33/68* | (2006.01) |
| *A61K 38/40* | (2006.01) |

(52) U.S. Cl.
CPC ............... *A61K 38/54* (2013.01); *C07K 14/515* (2013.01); *A61K 39/3955* (2013.01); *G01N 33/6854* (2013.01)
USPC ............. 514/2.3; 424/94.3; 514/2.4; 514/2.5; 514/2.6; 514/2.7; 514/2.8; 514/3.4

(58) Field of Classification Search
None
See application file for complete search history.

(56) References Cited

U.S. PATENT DOCUMENTS

| 4,900,673 | A | 2/1990 | Harper et al. |
|---|---|---|---|
| 4,966,964 | A | 10/1990 | Shapiro et al. |
| 5,171,845 | A | 12/1992 | Spik et al. |
| 5,270,204 | A | 12/1993 | Vallee et al. |
| 5,286,487 | A | 2/1994 | Vallee et al. |
| 6,172,040 | B1 | 1/2001 | Naidu |
| 7,074,759 | B2 | 7/2006 | Naidu |
| 7,125,963 | B2 | 10/2006 | Naidu |
| 7,601,689 | B2 | 10/2009 | Naidu |
| 7,956,031 | B2 | 6/2011 | Naidu et al. |
| 8,003,603 | B2 | 8/2011 | Naidu |
| 8,021,659 | B2 | 9/2011 | Naidu et al. |
| 8,309,080 | B2 | 11/2012 | Naidu et al. |
| 2007/0141101 | A1 | 6/2007 | Nugent et al. |
| 2008/0254018 | A1 | 10/2008 | Naidu |
| 2011/0200575 | A1 | 8/2011 | Naidu et al. |
| 2011/0286986 | A1 | 11/2011 | Naidu et al. |

OTHER PUBLICATIONS

González-Chávez et al, (International Journal of Antimicrobial Agents 33 (2009) 301.e1-301.e8).*

Acharya, et al. "Crystal Structure of Human Angiogenin Reveals the Structural Basis for its Functional Divergence from Ribonuclease," Proc. Natl. Acad. Sci. USA, vol. 91, pp. 2915-2919, Apr. 1994.

Hu, et al. A Putative Angiogenin Receptor in Angiogenin-Responsive Human Endothelial Cells, Proc. Natl. Acad. Sci. USA, vol. 94, pp. 2204-2209, Mar. 1997.

King, et al. Neovascularisation of the Meniscus with Angiogenin, An Experimental Study in Rabbits, The Journal of Bone and Joint Surgery, vol. 73-B, No. 4, pp. 587-590, Jul. 1991.

Maiti, et al. "Isolation and Characterization of an Angiogenin-Like Protein from Goat Plasma," Protein and Peptide Letters, vol. 9, No. 4, pp. 283-288, 2002.

Moroianu, et al. "Nuclear Translocation of Angiogenin in Proliferating Endothelial Cells is Essential to its Angiogenic Activity," Proc. Natl. Acad. Sci. USA, vol. 91, pp. 1677-1681, Mar. 1994.

R .Nagarajan, Langmuir 2000, 16, 6400-6415.

Strydom, "The Angiogenins," Cell. Mol. Life Sci., vol. 54, pp. 811-824, 1998.

Soncin, et al. "Interaction of Heparin with Human Angiogenin," The Journal of Biological Chemistry, vol. 272, No. 15, pp. 9818-9824, Apr. 11, 1997.

* cited by examiner

*Primary Examiner* — Bridget E Bunner
*Assistant Examiner* — Fozia Hamud
(74) *Attorney, Agent, or Firm* — Knobbe, Martens, Olson & Bear LLP

(57) ABSTRACT

Antimicrobial compositions based upon stabilized angiogenin compositions also contain osteopontin and antimicrobial proteins such as lactoperoxidase (LPO), myeloperoxidase (MPO), salivary peroxidase (SPO) and lysozyme.

13 Claims, 5 Drawing Sheets

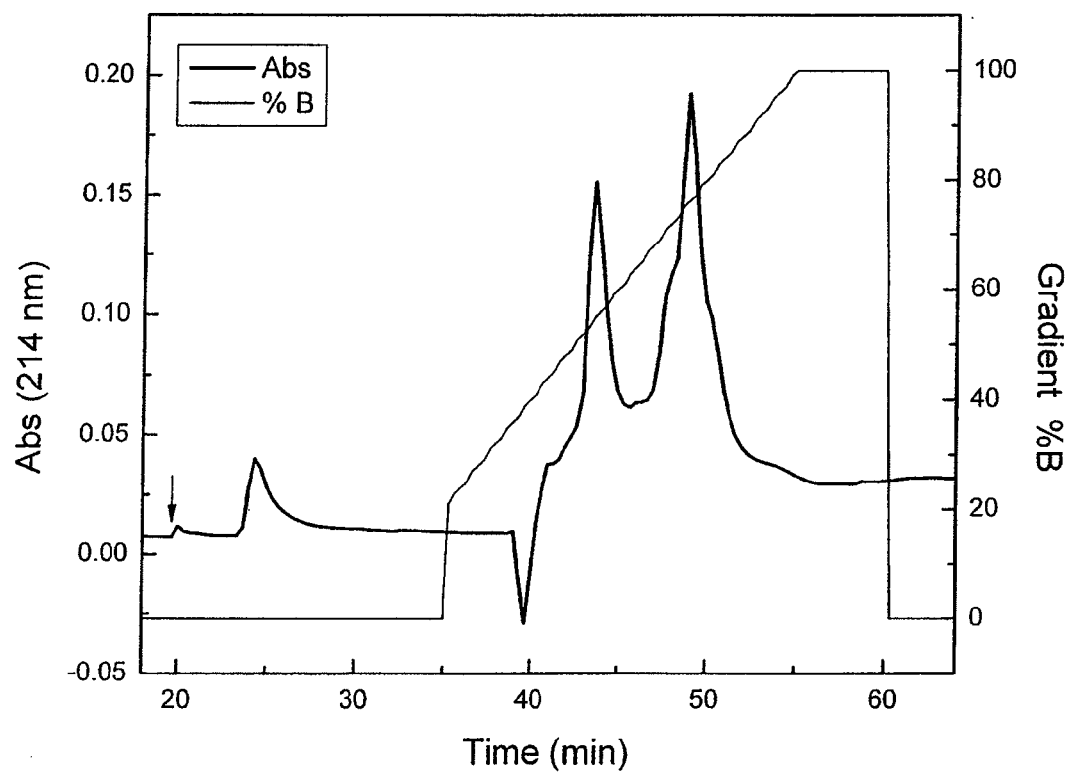
FIGURE-1: Isolation and purification of ANG

FIGURE-2: Biotinylated ANG–LF Interactions
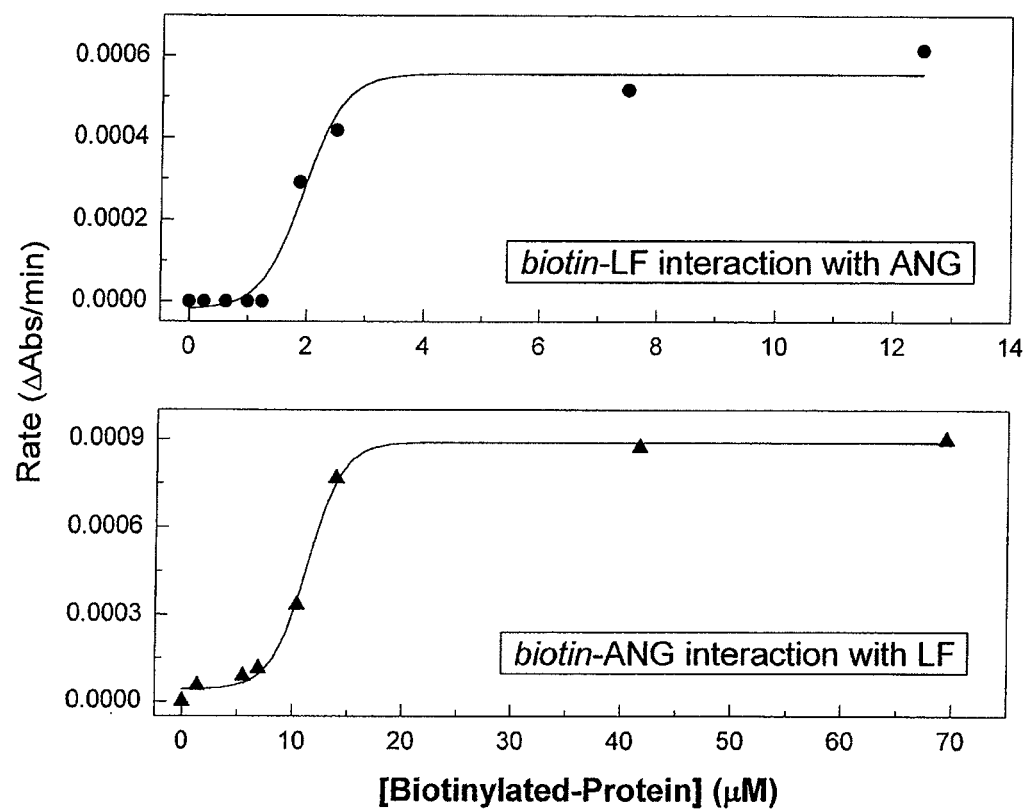

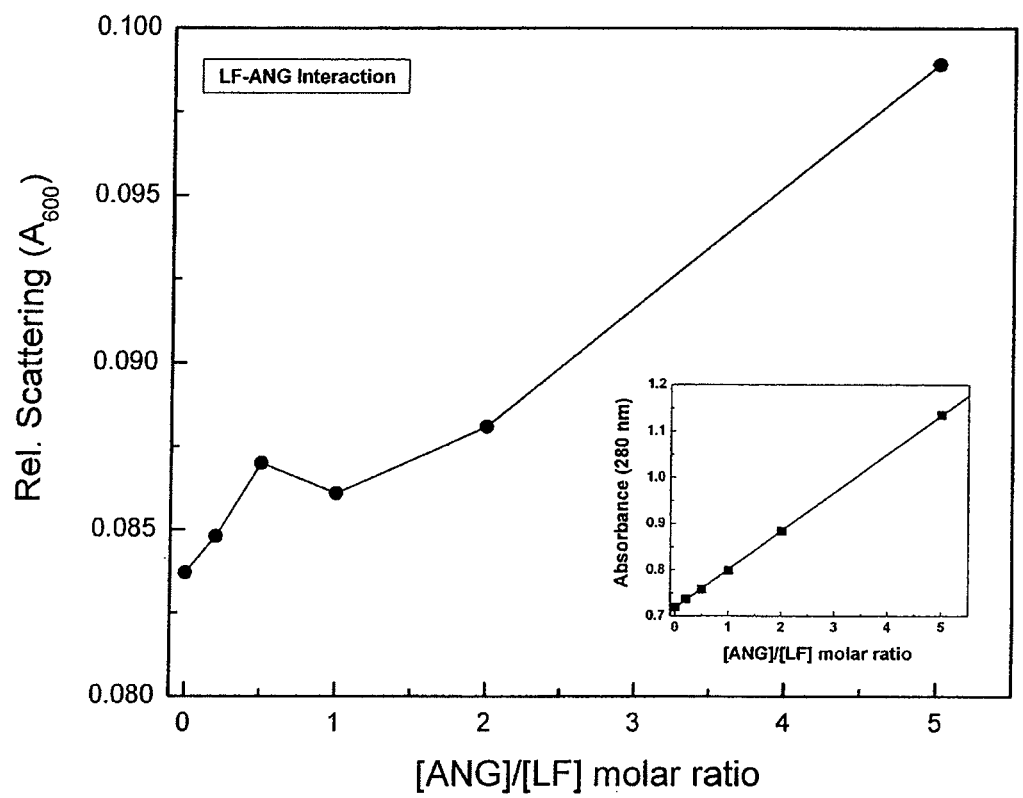
FIGURE-3: ANGex Detection by Turbidometry

FIGURE-4: Detection of ANGex formation
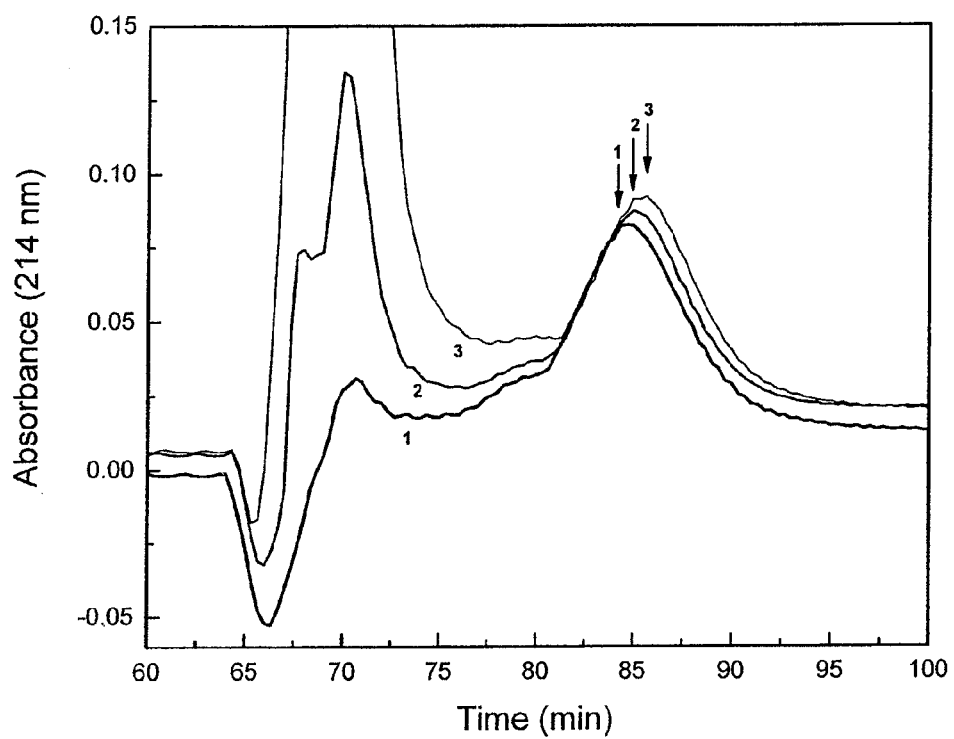

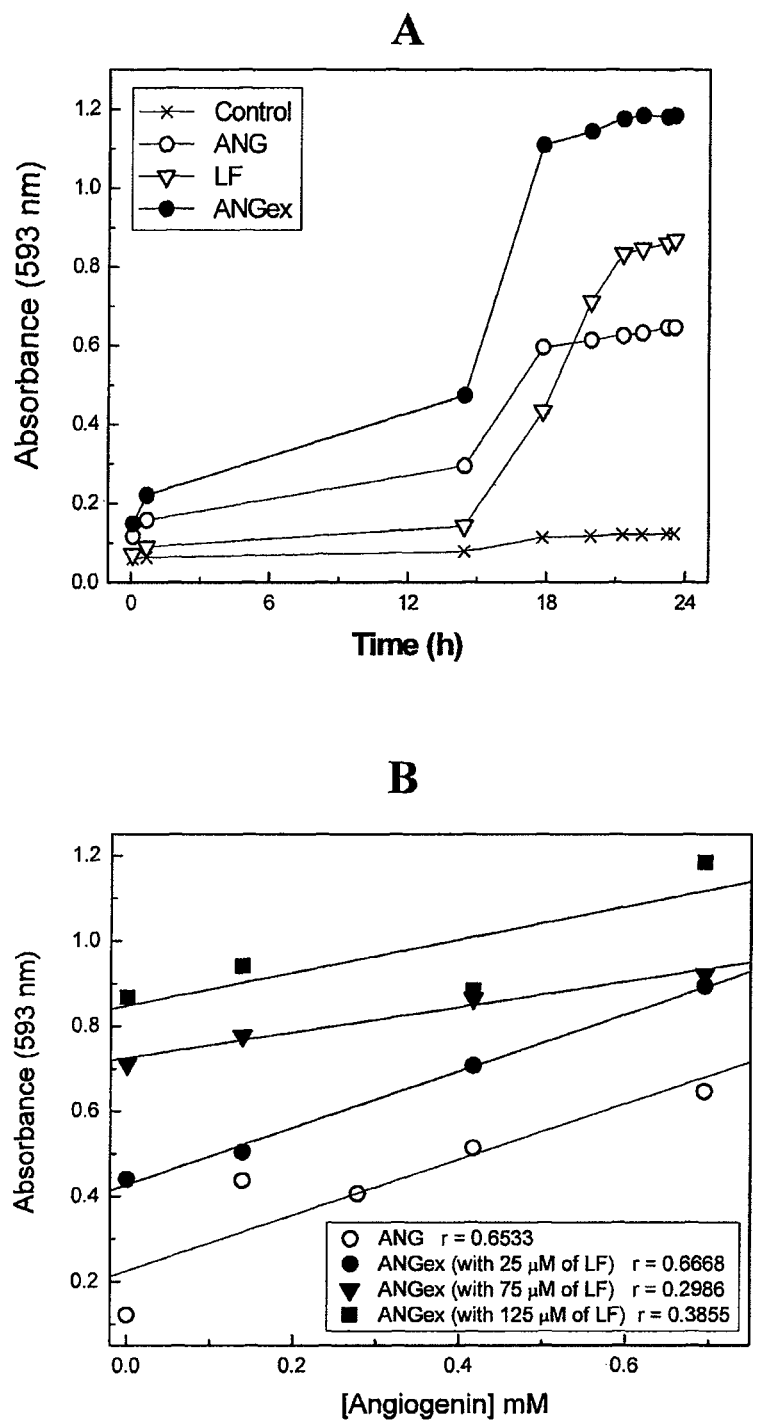

SEQUENCE LISTING

```
<160> NUMBER OF SEQ ID NOS: 1

<210> SEQ ID NO 1
<211> LENGTH: 124
<212> TYPE: PRT
<213> ORGANISM: Bos taurus

<400> SEQUENCE: 1

Ala Gln Asp Asp Tyr Arg Tyr Ile His Phe Leu Thr Gln His Tyr Asp
 1               5                  10                  15

Ala Lys Pro Lys Gly Arg Asn Asp Glu Tyr Cys Phe Asn Met Met Lys
            20                  25                  30

Asn Arg Arg Leu Thr Arg Pro Cys Lys Asp Arg Asn Thr Phe Ile His
        35                  40                  45

Gly Asn Lys Asn Asp Ile Lys Ala Ile Cys Glu Asp Arg Asn Gly Gln
    50                  55                  60

Pro Tyr Arg Gly Asp Leu Arg Ile Ser Lys Ser Glu Phe Gln Ile Thr
65                  70                  75                  80

Ile Cys Lys His Lys Gly Ser Ser Arg Pro Pro Cys Arg Tyr Gly Ala
            85                  90                  95

Thr Glu Asp Ser Arg Val Ile Val Val Gly Cys Glu Asn Gly Leu Pro
            100                 105                 110

Val His Phe Asp Glu Ser Phe Ile Thr Pro Arg His
            115                 120
```

ANTIMICROBIAL ANGIOGENIN COMPLEXES (ANGEX) AND USES THEREOF

RELATED APPLICATIONS

This application is a continuation of U.S. application Ser. No. 13/185,115, filed Jul. 18, 2011, now U.S. Pat. No. 8,440,183, issued May 14, 2013, which is a divisional of U.S. application Ser. No. 12/554,602, filed Sep. 4, 2009, now U.S. Pat. No. 8,003,603, issued Aug. 23, 2011, which is a divisional of U.S. application Ser. No. 11/734,729, filed Apr. 12, 2007, now U.S. Pat. No. 7,601,689 issued Oct. 13, 2009. All of the above listed applications are incorporated herein by reference in their entirety.

BACKGROUND OF THE INVENTION

1. Field of the Invention

The invention relates to protein stabilization, particularly stabilization of angiogenin by immobilization on natural substrates which includes but not limited to proteins, polysaccharides, lipids and polyphenols.

2. Description of the Related Art

Angiogenesis and vasculogenesis are two primary pathways in the development and maintenance of mammalian health. The angiogenic role is to supply and support tissue with ample vasculature, thus providing a route of access for the transportation of essential nutrients, including oxygen and the removal of metabolic waste in a sustained manner. Angiogenesis is a strictly regulated, multi-step process that occurs during normal physiology such as wound healing, pregnancy, and development.

Angiogenin (ANG) has been shown to be a key mediating factor in the underlying cascade of chemical events leading to angiogenesis, which makes it a very important precursor molecule for both muscle development and vascular generation. ANG is a 14-kDa, basic heparin-binding protein and a member of the pancreatic ribonuclease (RNase) superfamily. ANG can serve as a substrate for endothelial cell adhesion. ANG resembles pancreatic RNase-A; their amino acid sequences are about 35% identical, including the active site residues. An overview of the relationship of ANG and other RNases of the super-family showed that their genes all are in relative close proximity on human chromosome 14. However, human ANG shows a weak ribonucleolytic activity (lower by $10^4$ to $10^6$-fold) despite of its potent angiogenic function. The actions of ANG involve nearly all phases of angiogenesis (Strydom D J. *Cell Mol. Life. Sci.* 54:811-824, 1998; Acharya B et al., *Proc. Natl. Acad. Sci. USA* 91:2915-2919, 1994). When ANG was implanted into experimentally injured menisci of New Zealand white rabbits, localized neovascularization occurred in 52% of the treated animals as compared to 9% of controls (King T V et al., *J. Bone Joint Surg. Br.* 73(4):587-590, 1991). Mutant ANG proteins with enhanced angiogenic activity have also been reported (WO 89/09277). Site specific mutations in ANG resulted in mutant proteins with increased RNase and angiogenic activities (U.S. Pat. No. 4,900,673). Replacement of a specific section of ANG with a subsequence characteristic of RNase unexpectedly resulted in a mutant ANG/RNase hybrid with increased angiogenic activity (U.S. Pat. Nos. 5,286,487; 5,270,204).

ANG (RNase type-4 and RNase type-5 forms) is an active secretory protein found in milk. In cow's milk the concentrations are about 2 mg/L for RNase 4 and between 1 and 8 mg/L for RNase 5 (Ye X Y, et al., *Life Sci.* 67:2025-2032, 2000; Komolova G S, et al., *Appl. Biochem. Microbiol.* 38:199-204, 2002). ANG circulates in human plasma at a concentration of about 0.3 µg/mL with a fast turnover rate and a half-life <5 min. ANG can induce most of the events necessary for the formation of new blood vessels. It binds avidly to endothelial cells and stimulates cell migration and invasion. ANG promotes cell proliferation and differentiation; mediates cell adhesion and activates cell associated proteases; and also induces plasminogen activator and thereby, the plasmin system promoting migration and tubular morphogenesis of endothelial cells. Exogenous ANG is transported into the nucleus of endothelial cells. The nuclear translocation results in accumulation of the ANG in the nucleolus. Transportation of ANG from the cell surface into the nucleus and subsequently to the nucleolus is critical for its angiogenic activity. The import of ANG from the cytosol to the nucleus is signal-dependent, carrier mediated and energy-dependent, active transport process (Hu G F, et al., *Proc. Natl. Acad. Sci. USA* 94:2204-2209, 1997; Moroianu J, et al., *Proc. Natl. Acad. Sci. USA* 91:1677-1681, 1994).

ANG is a potent inducer of neo-vascularization and the only angiogenic molecule known to exhibit ribonucleolytic activity. Its overall structure, as determined at 2.4 Å, is similar to that of pancreatic RNase A, but it differs markedly in several distinct areas, particularly the ribonucleolytic active center and the putative receptor binding site, both of which are critically involved in biological function. Most strikingly, the site that is spatially analogous to that for pyrimidine binding in RNase A differs significantly in conformation and is "obstructed" by Gln-117. Movement of this and adjacent residues may be required for substrate binding to ANG and, hence, constitute a key part of its mechanism of action (Acharya K R, et al., *Proc. Natl. Acad. Sci. USA* 91:2915-2919, 1994; Russo N, et al., *Proc. Natl. Acad. Sci. USA* 91:2920-2924, 1994).

X-ray diffraction and mutagenesis results have shown that the active site of the human protein is obstructed by Gln-117 and imply that the C-terminal region of ANG must undergo a conformational rearrangement to allow substrate binding and catalysis. Two residues of this region, Ile-119 and Phe-120, make hydrophobic interactions with the remainder of the protein and thereby help to keep Gln-117 in its obstructive position. Furthermore, the suppression of activity by the intra-molecular interactions of Ile-119 and Phe-120 is counter-balanced by an effect of the adjacent residues, Arg-121, Arg-122 and Pro-123, which do not appear to form contacts with the rest of the protein structure. They contribute to enzymatic activity by constituting a peripheral sub-site for binding polymeric substrates. These results reveal the nature of the conformational change in human ANG and assign a key role to the C-terminal region both in this process and in the regulation of human ANG function (Russo N, et al., *Proc. Natl. Acad. Sci. USA* 93:3243-3247, 1996).

The pioneering work of Vallee and co-workers has paved the path in the development of health applications for human ANG. U.S. Pat. No. 4,727,137 discloses therapeutic use of human ANG to promote the development of hemo-vascular network, for example, to induce collateral circulation following a heart attack, or to promote wound healing, for example, in joints or other locations. This invention also describes diagnostic applications of human ANG in screening for malignancies. U.S. Pat. No. 4,952,404 describes healing of injured avascular tissue could be promoted by applying human ANG in proximity to the injured tissue.

Besides an angiogenic factor, ANG has been used in the treatment of viral infection such as HIV (WO 2004/106491A2). The RNase activity of ANG seem to be an inhibitor of viral replication.

Activation of the receptor for ANG has been proposed as a method to promote wound healing (WO 98/40487A1). A method of skin whitening by applying a composition containing ANG has been described (U.S. Pat. No. 5,698,185). ANG was first isolated from human carcinoma cells and subsequently from human plasma, bovine plasma, bovine milk, mouse, rabbit, and pig sera and goat plasma (Maiti T K, et al., *Prot. Pep. Lett.* 9:283-288, 2002) and its use to diagnose cancer has been suggested (WO 02/25286).

However, the exploitation of human ANG polypeptide for broad-spectrum human health-care (e.g., health supplementation, body building, cosmetics, oral health, post-operative wound care) and animal health applications (e.g., feed conversion for weight gains in meat-yielding animals) is limited without a mass supply of the compound. Such mass production of ANG requires an acceptable (preferably a food-grade) raw material source and an effective large-scale purification process for a high yield of ANG. Isolation of milk ANG from healthy dairy animals could provide an answer to this limitation.

Bovine Milk ANG

Spik and co-workers described a method to isolate ANG from mammalian milk. U.S. Pat. No. 5,171,845 discloses an extraction process for ANG from cow milk consisting of a delipidation step by centrifugation, chromatographic steps on SP-Sephadex® C50 and S-Sepharose® columns, followed by a gel filtration step on Bio-gel® P-30 column with a final fast protein liquid chromatography (FPLC) step on Phenyl Superose® HR5/5 column. The protein yield was estimated at 0.5 mg of ANG per liter of delipidated milk.

U.S. Pat. Nos. 6,010,698 and 6,268,487 disclose alternative processes for isolating ANG (their homologues and fragments) from mammalian milk or a milk derivative.

Bovine milk ANG is a single-chain protein of 125 amino acids; it contains six cysteines and has a calculated molecular weight of 14,595. Bovine milk ANG has 65% sequence homology with human plasma ANG and 34% homology with bovine pancreatic RNase A. The three major active site residues involved in the catalytic process, His-14, Lys-41 and His-115, are conserved in the bovine milk ANG with ribonucleolytic activity comparable to that of the human protein. Bovine milk ANG contains an additional cell recognition tri-peptide Arg-Gly-Asp, which is not present in the human ANG protein. In contrast to the human protein, the N-terminus of bovine ANG is unblocked. Two regions, 6-22 and 65-75, are highly conserved between human and bovine ANG proteins, but are significantly different from those of the RNases, suggesting a possible role in the molecules' biological activity. Bovine ANG has the following sequence: $NH_2$-Ala(1)-Gln-Asp-Asp-Tyr-Arg-Tyr-Ile-His-Phe(10)-Leu-Thr-Gln-His-Tyr-Asp-Ala-Lys-Pro-Lys(20)-Gly-Arg-Asn-Asp-Glu-Tyr-Cys-Phe-Asn-Met(30)-Met-Lys-Asn-Arg-Arg-Leu-Thr-Arg-Pro-Cys(40)-Lys-Asp-Arg-Asn-Thr-Phe-Ile-His-Gly-Asn(50)-Lys-Asn-Asp-Ile-Lys-Ala-Ile-Cys-Glu-Asp(60)-Arg-Asn-Gly-Gln-Pro-Tyr-Arg-Gly-Asp-Leu(70)-Arg-Ile-Ser-Lys-Ser-Glu-Phe-Gln-Ile-Thr(80)-Ile-Cys-Lys-His-Lys-Gly-Ser-Ser-Arg(90)-Pro-Pro-Cys-Arg-Tyr-Gly-Ala-Thr-Glu-Asp(100)-Ser-Arg-Val-Ile-Val-Val-Gly-Cys-Glu-Asn(110)-Gly-Leu-Pro-Val-His-Phe-Asp-Glu-Ser-Phe(120)-Ile-Thr-Pro-Arg-His-COOH (SEQ ID NO: 1). Disulfide bonds link Cys(27)-Cys(82), Cys(40)-Cys(93), and Cys(58)-Cys(108) (Maes P, et al., *FEBS Lett.* 241:41-45, 1988; Bond M D, et al., *Biochemistry* 28:6110-6113, 1989).

Molecular dynamics simulation (MDS) studies showed marked differences in the hydrogen-bonding patterns in the active site regions of the human and bovine ANG systems. Furthermore, the positions of water molecules identified in the crystal structures of human ANG significantly differ from that of the bovine ANG. Positioning of the water molecules in the protein structure play an important role in manifesting the subtle functional differences between human and bovine ANG systems (Madhusudhan M S, et al., *Biopolymers* 49:131-144, 1999).

Synthetic peptides corresponding to the C-terminal region of ANG inhibit the enzymatic and biological activities of the molecule, while peptides from the N-terminal region do not affect either activity. Several C-terminal peptides also inhibit the nuclease activity of ANG when tRNA is the substrate. Furthermore, peptide Ang(108-123) decreases the neo-vascularization elicited by ANG in the chick chorioallantoic membrane assay (Ryback S M, et al., *Biochem. Biophys. Res. Commun.* 162:535-543, 1989).

The mechanism of the angiogenic activity involves multiple interactions of ANG with various molecules through specific regions on its protein surface. The interactive molecules include heparin, plasminogen, elastase, angiostatin, actin and most importantly a 170-kilodalton receptor on subconfluent endothelial cells.

The interaction of ANG with heparin could protect the molecule from protein cleavage by trypsin hydrolysis. A basic 'triple' amino acid cluster on ANG, Arg-31/Arg-32/Arg-33, has been identified as the heparin binding site. Mutations of the triple cluster and of the Arg-70 residue could decrease the binding affinity of ANG to heparin as well as its cell adhesion property. However, a replacement of any other basic residues in the polypeptide chain does not affect the heparin binding property of ANG. The heparin binding site on ANG is outside the catalytic center. Light scattering measurements on ANG-heparin mixtures suggest that a single heparin chain (mass of 16.5 kDa) could interact with approximately 9 ANG molecules (Soncin F, et al., *J. Biol. Chem.* 272:9818-9824, 1997).

Several bio-molecules in milk and other exocrine secretions avidly bind to heparan sulfate, the active constituent of "mucin" that overlay the intestinal epithelia. The heparan sulfate interaction is generally mediated by cationic domains located in the N-terminus region of such bio-molecules. These immobilization processes facilitate retention of biological compounds on epithelial surface and could possibly "activate" these molecules for specific physiological functions, including their internalization and bioavailability. Accordingly, heparan sulfate and its analogues have a widespread application in chromatography as column matrices, for purification and isolation of several milk compounds, including ANG, lactoferrin, lactoperoxidase and other bioactive peptides.

U.S. Pat. No. 6,172,040 describes a method for immobilization of milk lactoferrin (LF) on a galactose-rich polysaccharide (GRP) substrate, which is analogous to the heparan sulfate. This immobilization process involved the interaction of GRP with a highly cationic N-terminus domain of LF, as expected. The immobilization process described in this invention caused a significant increase in the antimicrobial activity of LF, and also provided a structure-conformational stability to the protein molecule.

The binding of ANG to heparan sulfate via its cationic N-terminus domain, its mitogenic characteristics and occurrence in different physiological milieu such as milk, plasma, other exocrine secretions and tissue sites, is in striking proximity to LF. On a speculative basis, the immobilization methods for LF, which are disclosed in U.S. Pat. No. 6,172,040, when adapted and applied to ANG, this angiogenic milk protein has demonstrated a unique molecular and functional behavior.

SUMMARY OF THE INVENTION

The present invention relates to immobilized ANG complexes (ANGex) and mixtures of ANGex and free dispersed native (fdn)-ANG having preserved, enhanced and specific biological activity. ANG is immobilized on naturally occurring substrates, preferably via the N-terminus region of the ANG. Suitable substrates include proteins, polysaccharides, cellulose compounds, nucleic acids, nucleotides, lipids and metallic compounds. Preferred substrates include collagen, gelatin, fibronectin, casein, mucin, heparin-sulfate, carrageenan, gums/galactans, pectins, deoxyribonucleic acid, adenosine triphosphate or a triglyceride, galactose-rich polysaccharide (GRP), vitamin-E, ceruloplasmin, metallothionein and lactoferrin (LF) being most preferred.

Embodiments of the invention are directed to compositions which include an isolated angiogenin non-covalently complexed to an isolated naturally occurring substrate.

In preferred embodiments, the angiogenin is isolated from a biological fluid. Preferably, the biological fluid is colostrum, milk, whey, milk serum, blood, plasma or serum. Preferably, the biological fluid is obtained from a mammal which is selected from humans, cows, buffalos, horses, sheep, pigs and camels. In some embodiments, the mammal is genetically modified.

In preferred embodiments, the substrate includes proteins such as transport proteins, subepithelial matrix proteins, or antimicrobial proteins. Preferably, the transport protein is lactoferrin, transferrin, ovo-transferrin (conalbumin), ceruloplasmin or transfer factors. Preferably, the subepithelial matrix protein is fibronectin, fibrinogen, laminin, vitronectin, osteopontin, native collagens or denatured collagen (gelatin). Preferably, the antimicrobial protein is selected from peroxidases (lacto, myelo and salivary forms) and lysozyme.

In some preferred embodiments, the substrate includes triglycerides.

In some preferred embodiments, the substrate includes a coenzyme such as coenzyme-Q10 (ubiquinone) or NADH.

In some embodiments, the substrate includes a vitamin such as vitamins A, C and/or E.

In some embodiments, the substrate includes a nucleic acid such as single and double stranded DNA and RNA. In some embodiments, the substrate includes a nucleotide such as ATP, CTP, GTP or TTP.

Embodiments of the invention are directed to methods of preparing angiogenin complexes by mixing the angiogenin with a substrate in a liquid medium. In preferred embodiments, the substrate includes a protein such as transport proteins, subepithelial matrix proteins and antimicrobial proteins. Preferably, the transport protein includes lactoferrin, transferrin, ovo-transferrin (conalbumin), ceruloplasmin and/or transfer factors. Preferably, the subepithelial matrix protein includes fibronectin, fibrinogen, laminin, vitronectin, osteopontin, native collagens and/or denatured collagen (gelatin). Preferably, the antimicrobial protein is selected from peroxidases (lacto, myelo and salivary forms) and lysozyme.

In some embodiments, the substrate includes triglycerides.

In preferred embodiments, the liquid medium comprises water.

Embodiments of the invention are directed to compositions that include complexed angiogenin and native angiogenin. Preferably, the composition includes complexed angiogenin and native angiogenin at a ratio of 1:1 to 1:10. More preferably, the composition also includes a buffer system, a physiological acceptable base and a salt. Preferably, the buffer system is oxalic acid, ethylenediamine tetraacetic acid or citric acid. Preferably, the physiological acceptable base is sodium bicarbonate. Preferably, the salt is sodium chloride, potassium chloride or calcium chloride.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 1: Isolation and Purification of ANG

Isolation of ANG using cation-exchange chromatography (UNO S6 column) with NaCl gradient (20% to 100% B) in 20 min. The time of injection of ANG sample (1 mL of 0.2 mg/mL in 20 mM sodium phosphate buffer pH 7.2) is indicated by the arrow. ANG eluted as two separate peaks at 39 min. (38% Buffer B) and 44.5 min. (60% Buffer B) respectively, from the time of injection. ANG was detected by monitoring the absorbance at 214 nm using a UV-Vis detector.

FIG. 2: Biotinylated ANG-LF Interactions

Interaction of biotinylated LF and biotinylated ANG with immobilized ANG (●) and immobilized LF (▲) was measured by kinetic ELISA. ANG immobilized on a microtiter plate was incubated with biotinylated LF, vice versa; LF immobilized on a microtiter plate was incubated with biotinylated ANG, respectively. Unbound proteins were removed by thorough washing with PBS-Tween buffer and the bound proteins were subjected to an enzymatic reaction with avidin-alkaline phosphatase. The dose dependence of rate of turnover of p-nitrophenyl phosphate substrate by avidin-alkaline phosphatase on the concentration of biotinylated protein indicated the interaction between LF and ANG.

FIG. 3. ANGex Detection by Turbidometry

Turbidity titration for the detection of ANGex in solution involved measurement of A600 for a series of LF solutions to which increasing amounts of ANG was added. The relative light scattering as measured by the absorbance at 600 nm, plotted against the molar concentration ratio of ANG to LF indicated non-linear increase in macromolecular size due to complex formation. Inset shows linear increase of A280 for the same series of solutions.

FIG. 4. Detection of ANGex Formation

Cation-exchange chromatogram is shown for the presence of ANGex, eluted using 1 M NaCl gradient of (60-100% B in 80 min) and monitored by the absorbance at 214 nm. (fdn)-LF (1 mg/mL) elutes as a single peak at retention time of 84.6 min (Curve 1). The retention time of this peak increases upon ANGex formation with 1 mg/mL (Curve 2) and 4 mg/mL (Curve 3) of ANG.

FIGS. 5A and B. Antioxidant Activity of ANG, LF and ANGex

Antioxidant activity was determined by FRAP assay with Vitamin C, TROLOX and $FeSO_4$ as standards, by following the increase in absorbance at 593 nm with time. FIG. 5A shows the FRAP reaction kinetics data for LF, ANG and ANGex. The concentrations of the three standards, LF, ANG and ANGex were 10 mg/ml (125 μM for LF, 694 μM for ANG). FIG. 5B compares the antioxidant efficiency (r) as measured by the change in absorbance with the concentration of ANGex. Lines represent ANGex formed at varying concentrations of ANG with 0 (○), 2 (●), 6 (▼) and 10 mg/mL (■) of LF. ANGex formed with 2 mg/mL of LF exhibits the highest antioxidant efficiency with r=0.046.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Suitable ANG can be isolated from dairy sources including colostrum, milk, whey and milk serum from humans, cows, buffalos, horses, sheep, pigs or camels. Additionally, ANG also can be purified from other biological fluids from animals (eg. blood), recombinant sources and genetically-modified organisms (GMOs). Recombinant ANG may be cloned-expressed in either prokaryotic or eukaryotic cellular systems. The ANG is isolated by any conventional method, such as by filtration methods, chromatography techniques using ion-exchanger, molecular-sieve or affinity columns.

Dietary supplementation with ANG may be helpful to individuals suffering from vascular disorders such as congestive heart failure, myocardial infarction, stroke, stable and unstable angina, poor circulation, for supportive supplementation of long-term medications in the management of hypertension, hyperlipidemia, diabetes, and chronic fatigue syndrome; mitochondrial diseases including mitochondrial encephalomyopathy, lactic acidosis, and stroke-like symptoms, Kearns-Sayre syndrome and Alpers' disease.

ANG supplementation supports vascular health and promotes repair of damaged or clogged vascular tissue. However, in order to function properly, the structure of ANG must be stabilized.

The activity of ANG, like the activity of most proteins, is highly dependent on the three-dimensional or tertiary structure of the protein. If the protein does not have the proper conformation its activity is diminished or lost. ANG's instability limits it usefulness. Milieu conditions such as metals (copper in particular), carbonic ions, salts, pH and conductivity affect the angiogenic properties of ANG. In addition, protein isolation procedures, storage, freezing-thawing, can adversely affect the biofunctionality of ANG. Consequently, before ANG can be used for commercial application, it would be expected to become denatured or inactivated. (Soncin F, et al. *Biochem Biophys Res Comm* 236:604-610, 1997)

Embodiments of the invention are directed to providing a stabilized form of ANG. ANG is immobilized on naturally occurring substrates. Suitable substrates include polysaccharides, proteins, lipids, nucleic acids, nucleotides, and vitamins. Preferred substrates include heparan sulfate, carrageenan, mucin, collagen, gelatin, fibronectin, transferrin, conalbumin, lysozyme, peroxidase, triglycerides, and vitamins. Galactose-rich polysaccharide (GRP), vitamin-E, ceruloplasmin, metallo-thionein and lactoferrin being the most preferred.

The attachment of ANG to the substrate may be non-covalent or covalent binding. The interaction may be at the N-terminus, the C-terminus or any molecular region or site of the ANG protein. In some embodiments, ANG is attached covalently to a polysaccharide, preferably a galactose-rich polysaccharide by covalent attachment to the N-terminus of ANG. In other embodiments, the complex is formed by a non-covalent association between ANG and a protein, lipid, nucleic acid, vitamin or carbohydrate molecule. The basis of the association may be electrostatic or by hydrophobic interaction or using bifunctional reagents.

ANG is immobilized on a naturally occurring substrate. Such substrates include organic compounds, which attach to the N-terminus domain of the ANG protein. Most preferably, the substrate is a galactose-rich polysaccharide. Suitable galactose-rich polysaccharides include galactose derivatives comprising galactose, anhydrogalactose, 2-O-methyl-galactose, and 4-O-methyl-galactose, among others. The GRP substrates can be purchased or extracted from commercial agars by known methods. Other suitable biologically active substrates include proteins, such as collagen, denatured collagen (gelatin), fibronectin, and casein; polysaccharides, such as mucin, heparan sulfates, carrageenan, and cellulose; nucleic acids and their nucleotides, such as deoxyribonucleic acid and adenosine triphosphate; and lipids such as triglycerides.

ANG is immobilized on the substrate using any suitable technique. For example, ANG can be immobilized simply by mixing the ANG with the biologically active substrate in a suitable medium, such as deionized water. The immobilization process is dependent on the quality of the substrate as well as the quality of the ANG. Consequently, the amount of substrate and the amount of ANG to be used in the immobilization reaction will depend, inter alia, on the choice of starting materials. The immobilization technique and the amounts of substrate and ANG will be readily determinable by a skilled artisan without undue experimentation.

ANG complexes could be formed with a second protein based on functional association or a synergy that may enhance ANG function. The ANG protein complexes could be formed by physical, charge and/or chemical interactions. ANG and a protein substrate may be complexed together directly or they may be complexed by means of an appropriate bifunctional reagent. A non-covalent complex may be formed by means of electrostatic interactions which may be enhanced by inclusion of appropriate buffers and/or salts.

Embodiments of the invention include methods such as biotin-avidin binding and disulfide bonding. The ANG polypeptide chain consists of 6 cysteine residues that form 3 disulfide bonds at 26-81, 39-92, and 57-107 residue positions. ANG may be labeled with biotin and mixed with a substrate protein associated with avidin to form a complex by association of the biotin with the avidin. Alternatively, the ANG may be attached to avidin and the biotin complexed onto the substrate protein.

The formation of a complex may be confirmed by using co-immunoprecipitation techniques. In preferred embodiments, the protein substrate is from the group including, but not limited to transport proteins, subepithelial matrix proteins and antimicrobial proteins. Transport proteins include but are not limited to lactoferrin, transferrin, ovo-transferrin (conalbumin), ceruloplasmin, metallo-thionein and transfer factors. Subepithelial matrix proteins include but are not limited to fibronectin, fibrinogen, laminin, vitronectin, osteopontin, native collagens and denatured collagen (gelatin). Antimicrobial proteins include but are not limited to peroxidases (lacto, myelo and salivary forms) and lysozyme.

Embodiments of the invention are directed to ANG complexed with lipids. ANG may be formed into a complex with CoQ-10 by physical and/or chemical interactions. ANG and CoQ-10 may be complexed together directly or they may be complexed by means of an appropriate bifunctional reagent. A non-covalent complex may be formed by means of electrostatic interactions which may be enhanced by inclusion of appropriate buffers and/or salts.

In some embodiments, ANG is incorporated into anionic lipid films by electrostatic interactions. ANG may be complexed into micro-emulsions. Lipids used to form such films and micro-emulsions include triglycerides, phospholipids including commercially available preparations such as Phospholipid Lipoid S 100 (Lipoid KG, Germany), lipophilic vitamins such as Coenzyme-Q10, Vitamin A, Vitamin E and Ubiquinone. Other Vitamins which complex with ANG include nicotinamide adenine dinucleotide (NADH) and Ascorbic acid. More preferably, the phospholipid is one or more selected from Docosahexaenoic acid (DHA), phosphatidyl glycerol, phosphatidyl inositol, phosphatidyl serine, phosphatidyl choline, phosphatidyl ethanolamine, phosphatidic acids, ceramides, cerebrosides, sphingomyelins and cardiolipins.

Nucleic acid/nucleotide-based ANG complexes may be formed based upon electrostatic interations between the positively charged ANG and the negatively charged DNA or RNA. The formation of such complexes is confirmed by Gel Mobility Shift Assay (Bading H. *Nucleic Acid Research* 16: 5241-5248, 1988).

In an embodiment of the present invention, ANG may be combined with metal ions such as copper and zinc, preferably copper.

In some embodiments, ANG is used as an aqueous solution containing a mixture of the ANGex and native ANG, where the concentration of the mixture in the solution is from about 0.001 to about 2.5% wt/vol and the ratio of ANGex to native ANG in the mixture is from about 1:1 to about 1:10, preferably about 1:1 to 1:5, and most preferably about 1:1. And in some embodiments, the mixture contains about 1% wt/vol ANGex and about 1% wt/vol native ANG.

In some embodiments, the aqueous solution further includes a buffer system that contains a physiologically acceptable acid, such as oxalic acid, ethylenediamine tetraacetic acid, and citric acid, preferably citric acid, a physiologically acceptable base, preferably sodium bicarbonate, and a physiologically acceptable salt, such as calcium chloride, potassium chloride and sodium chloride, preferably sodium chloride. The molar ranges of acid:base:salt is generally about 0.1 to 0.0001M (acid):1 to 0.001M (base):10 to 0.01M (salt); with 0.01-0.001M (acid):0.1 to 0.01M (base):1 to 0.01M(salt), preferred; and 0.001M (acid):0.01M (base):0.1M(salt), most preferred.

ANG useful in accordance with the present invention includes ANG isolated from mammalian sources (humans, cows, sows, mares, transgenic animals and the like), biological secretions such as serum, colostrum, transitional milk, matured milk, milk in later lactation, and the like, or processed products thereof such as skim milk and whey. Also useful is recombinant ANG cloned-expressed in either prokaryotic and eukaryotic cells. ANG is isolated by any conventional method, such as by chromatography, ion-exchanger, molecular-sieve or affinity column. In a preferred embodiment, ANG is isolated from plasma, serum, milk or a milk product. Despite their low abundance, ANG is easily isolated from milk or serum because it is more basic than other RNases. In a particularly preferred embodiment, ANG is co-isolated with lactoferrin from milk or milk product (Bond, et al., *Biochemistry* 27:6282-6287, 1988). The ANG/lactoferrin isolate is then stabilized as described herein.

Without intending to be limited by a theory of operation, it is believed that immobilization gives structural stability and bio-functional specificity to ANG. It is expected that ANGex molecules will demonstrate a molecular orientation similar to its orientation when adhered to endothelial and fibroblast cells when forming the extra-cellular matrix which is part of the angiogenic process. This property facilitates the retention and carry-through of ANG.

In preferred embodiments, the ANGex is combined with native ANG. The molecular ratio of ANGex versus native ANG is important in the specificity, broad-spectrum activity, and molecular stability of both the immobilized and the native ANG. Mixtures of ANGex and native ANG in a ratio of from about 0.25:1 to about 1:10, preferably from about 1:1 to about 1:2 of native ANG to ANGex, most preferably 1:1 ratio are preferred.

Mixtures of ANGex and native ANG are formed by adding excess ANG to the substrate. In a representative embodiment, from about 0.001% wt/vol to about 2.5% wt/vol, preferably from about 0.5% wt/vol to about 2.0% wt/vol, most preferably about 1% wt/vol of ANG is added to a solution containing 0.01% wt/vol galactose-rich polysaccharide.

In a preferred embodiment, the aqueous solution is buffered with a combination of a physiologically acceptable acid, such as oxalic acid, ethylenediamine tetraacetic acid, or citric acid, preferably citric acid, a physiologically acceptable base, preferably sodium bicarbonate, and a physiologically acceptable salt such as calcium chloride, potassium chloride or sodium chloride, preferably sodium chloride. The citrate and bicarbonate ratio in the buffer is significant for co-coordinated metal binding properties of ANG. The molar ranges of acid:base:salt is typically about 0.1 to 0.0001M (acid):1 to 0.001M (base):10 to 0.01M (salt); with 0.01-0.01M (acid): 0.1 to 0.01M (base):1 to 0.1M(salt), preferred; and 0.001M (acid):0.01M (base):0.1M(salt), most preferred.

ANGex may be substituted for ANG for any treatment for which ANG is useful. ANGex brings the added benefits of increased stability for ANG as an active agent. Because of the increased stability, ANGex has increased residence time compared to ANG so that both dosage and frequency of administration is less than with ANG.

ANGex is useful to improve cardiovascular function due to its well known ability to promote formation of new blood vessels. In addition, ANGex has antimicrobial and antioxidant properties as shown herein.

ANGex may be useful in treatment of cardiovascular disease, gastrointestinal disorders, maintenance of bone and joint health, maintenance of cognitive health, oropharyngeal health. ANGex may have cosmetic uses such as hair growth and regeneration, anti-aging, reduction of wrinkles and age spots, and skin rejuvenation. ANGex may be useful in the treatment of acne and other skin disorders including folliculitis, furunculosis, and TED. ANGex may be useful in postoperative recovery including surgical wound repair/healing, tissue resurfacing, and plastic surgery, both cosmetic and reconstructive. ANGex may be useful as a coating on biomaterials including sutures, implants, indwelling catheters and dental floss. ANGex may also be useful in veterinary practices and for increasing weight gain in meat animals.

EXAMPLES

Example-1

Angiogenin (ANG) Preparations

Bovine milk (6% fat, 3% protein) was concentrated 2-3 fold, by ultra-filtration through a polysulfonic membrane (pore size 30 kDa). ANG was isolated from the ultra-filtrate by precipitation of proteins with ammonium sulfate, followed by cation-exchange chromatography as previously described (Fedorova T V, et al., *Appl. Biochem. Microbiol.* 38:193-196, 2002). Briefly, the protein precipitated with 60% ammonium sulfate was dissolved in 0.01 M potassium phosphate buffer (pH 6.7) and dialyzed against the same buffer at 4° C. for 36 h. The dialysate was loaded on to a CM-cellulose 52 column (Serva, Germany) and 4-mL fractions were collected. Fractions with A280 ≥0.1 were pooled and dialyzed against 10 mM Tris-HCl buffer (pH 8.3). The dialyzate was then loaded on a CM-Toyopearl 650 S column (Tosoh, Japan) equilibrated with 0.05 M Tris-HCl buffer (pH 8.3). Column-bound proteins were eluted with a linear gradient of KCl concentration in the same buffer at a flow rate of 0.5 mL/min. ANG-containing fractions were further pooled, dialyzed against a 0.01 M potassium phosphate buffer (pH 7.0), and freeze-dried.

Furthermore, a second preparation of bovine milk ANG (mixture of RNAse type-4 and -5 proteins) obtained from Tatua Nutritionals (Morrinsville, New Zealand) was also used in the immobilization experiments. This second preparation of ANG (initially enriched from skim milk along with all other positively charged milk proteins) was isolated by cation-exchange chromatography. The column bound proteins were eluted step-wise by using various concentrations of salt (NaCl). The ANG-rich fraction was de-salted and concentrated by ultra-filtration. This ANG-rich preparation demonstrated >40% RNAse activity. For experimental purposes, the ANG-rich fraction was further purified to a higher level of purity, as follows: the ANG-rich fraction was run on a second type of cation-exchange column and protein was eluted with increasing concentrations of NaCl and by increasing the pH. This process separated ANG into (RNAse 4)-rich and (RNAse 5)-rich fractions, which were ultra-filtered and freeze-dried into powder form.

The purity and homogeneity of both lab-scale and pilot-scale ANG preparations was assessed by cation-exchange chromatography. The sample was loaded on to a UNO S6 column (Bio-Rad) equilibrated with 20 mM sodium phosphate buffer at pH 7.2. After extensive washing with the same buffer, ANG was eluted from the column by a gradient flow of 20 mM sodium phosphate buffer containing 1 M sodium chloride (20 to 100% in 20 min). Molecular weight of ANG (17 kDa) was confirmed by SDS-PAGE.

FIG. 1 depicts the isolation and purification of ANG using UNO S6 cation-exchange column. The time of injection of ANG sample (1 mL of 0.2 mg/mL in 20 mM sodium phosphate buffer pH 7.2) is indicated by the arrow. ANG eluted as two separate peaks at 39 min. (38% Buffer B) and 44.5 min. (60% Buffer B) respectively, from the time of injection. ANG was detected by monitoring the absorbance at 214 nm using a UV-Vis detector.

Reconstitution of ANG Protein in Buffered Solutions

For immobilization on different substrates, ANG was reconstituted into solution at a protein concentration of 1 mg/mL. The following different buffer solutions compatible with the chemical nature of the immobilization/conjugation substrates were used: i) carbohydrate-based support systems, 0.1 M sodium bicarbonate buffer [with 0.5 M NaCl (pH 8.3)]; ii) protein-based support systems, 20 mM sodium phosphate buffer (pH 7.2) or citrate-bicarbonate buffered saline [(CBS), pH 8.0; consisting of 1 mM citric acid, 10 mM NaHCO$_3$, and 100 mM NaCl]; and iii) lipid-based support systems, 50 mM sodium phosphate buffer (pH 7.0).

Preparation of Biotinylated ANG Reagents

ANG was biotinylated using biotin disulfide N-hydroxysuccinimide ester (Sigma), which contains an active ester to react with the primary amine of ANG. This reagent was dissolved in N,N-dimethylformamide at a concentration of 25 mg/mL. ANG (20 mg) was dissolved in 2 mL of 0.1 M sodium phosphate buffer, pH 7.6 to give a final concentration of 10 mg/mL. Reagent solution (volume: 0.4-mL volume) was slowly stir-mixed with the ANG solution, such that a 15 molar excess of reagent is present in the mixture. The mixture was gently agitated on a rocker for an hour at room temperature. The biotinylated protein was separated from excess reagent by gel filtration on a Sephadex G-25 column. The column was equilibrated with 10 mM PBS containing 138 mM NaCl and 2.7 mM KCl at pH 7.4. The mixture was loaded on to the column and washed with few drops of PBS. Biotinylated ANG (b-ANG) was eluted with PBS in 0.5 mL fractions monitoring the A280 of the eluent to confirm the presence of b-ANG. All the b-ANG fractions were pooled, its concentration was determined by Bradford assay and the degree of biotinylation was estimated by HABA/Avidin Assay.

Example-2

Preparation of ANGex Using Carbohydrate-Based Substrates

ANG is immobilized on carbohydrate-based supports using reductive amination process that involves reactive aldehyde groups generated by partial hydrolysis of agarose (or agar). Acid hydrolysis of agar under mild conditions leads to cleavage of glycosidic bonds between C-1 of 3,6-anhydro-L-galactose and O-3 of D-galactose residues that exposes D-galactosyl residues and leads to the formation of galactose-rich polysaccharides (GRP) (Gray G. Arch. Biochem. Biophys. 163:426-428, 1974; Lee R T, et al., Biochemistry 19:156-163, 1980).

Galactose-rich polysaccharide (GRP), extracted as a water-soluble fraction from agar was used as the substrate for ANG immobilization. GRP was prepared by adding 1-g of bacteriological agar (Difco) to 10-mL of citrate-bicarbonate buffered saline [(CBS), pH 8.0; consisting of 1 mM citric acid, 10 mM NaHCO$_3$, and 100 mM NaCl]. After thorough mixing on a vortex, the mixture was centrifuged for 2 min at 2500 rpm to obtain the GRP supernatant. The clear GRP solution was carefully aspirated and used as the substrate for ANG immobilization.

Other suitable polysaccharide substrates for ANG immobilization include sulfated glycosaminoglycans (GAG), i.e. heparin and heparan sulfate; various types of carrageenan substrates, i.e., Satiagel® brands (Degussa) ADG-14 (kappa/iota-type), ADF-23 (kappa/iota-type), DF-52 (iota-type); Genulacta® brand (Hercules) 1M K-100 (kappa-type); and Carravisco® brand DFL-1 (lambda-type). The binding mechanism is a simple electrostatic interaction between the positive amino groups on the ANG protein and the negative sulfate groups of the GAG and carrageenan.

Accordingly, a carbohydrate substrate (i.e. GRP, carrageenan, GAG or agarose) is thoroughly washed in distilled water, suspended in 0.2 M HCl (2-3 mL/g moist gel) with gentle agitation. After incubation at 55° C. for 3 h, the gel suspension is neutralized with dibasic sodium phosphate (0.2 M) solution, and washed with sodium phosphate (0.1 M) buffer at pH 7.2. The moist gel is filtered by gentle suction, weighed and reconstituted to a known concentration in buffer (ca. 75 mg/mL). The partially hydrolyzed gel is stored on ice and used within 3 hours of preparation. ANG (protein concentration: 1 mg/mL) was dissolved in 0.1 M sodium bicarbonate buffer with 0.5 M NaCl, pH 8.3. For immobilization, a 4 mL suspension containing 0.3 g moist gel in buffer solution was mixed with ANG solution and 6 mL of 100 mg/mL cyanogen bromide solution in Dioxan (150 mg of CNBr/mL of Sepharose®). The reaction mixture was gently agitated at 25° C. for 1 h, loaded on to a column and the gel (or beadlets) was extensively washed with coupling buffer (at least 5-6 column volumes) until no more amino groups (or excess protein) was detected in the washings.

In another method, 0.3 g of moist gel was suspended in 4 mL of buffer and was mixed with ANG solution and freshly prepared sodium cyanoborohydride solution (80 mM). The mixture was agitated at room temperature for 2 h and loaded on to a column and the gel (or beadlets) was extensively washed with coupling buffer (at least 5-6 column volumes) until no more amino groups (or excess protein) was detected in the washings.

In order to block any remaining active groups, the gel is transferred to 10 mL of 0.1 M Tris-HCl buffer, pH 8.0 and allowed to stand for 2 h. The gel (or beadlets) was washed again with 3 alternative cycles of high and low pH buffers. Each wash cycle consisted of at least 5 column volumes of 0.1 M acetic acid/sodium acetate, pH 4.0 containing 0.5 M NaCl; followed by a wash with 5 column volumes of 0.1 M Tris-HCl, pH 8.0 containing 0.5 M NaCl. This procedure ensured that no free ligand (ANG) bound non-specifically to the gel.

Example-3

Preparation of ANGex Using Protein-Based Substrates

ANG was immobilized on protein substrates via non-covalent interactions and conjugation methods including biotin-avidin affinity binding and disulfide bonding techniques. Suitable functional protein substrates: i) physiological transport-proteins including but not limited to lactoferrin, transferrin, ovo-transferrin (conalbumin), ceruloplasmin, metallothionein and transfer factors; ii) sub-epithelial matrix proteins including but not limited to fibronectin, fibrinogen, laminin, vitronectin, osteopontin, native collagens and denatured collagen (gelatin); iii) antimicrobial proteins including but not limited to peroxidases (lactoperoxidase, LPO; myeloperoxidase, MPO; and salivary peroxidase, SPO) and lysozyme.

Measurement of Biotinylated-ANG and LF Interactions by ELISA.

For binding studies, a 1% LF substrate (cow milk protein isolate) was prepared in 20 mM sodium acetate buffer (pH 4.0). A 1% LF solution (volume: 0.1-mL) was added to each well of a microtiter plate (Corning Costar® 3690) and allowed for an overnight surface adsorption at 4° C. The microplate was washed extensively with acetate buffer to remove any unbound LF. A 0.5% Tween (in PBS) was added to each well to block any unbound surface. Various concentrations (ranging 0 to 1 mg/mL) of biotinylated ANG solution (in 20 mM PBS, pH 7.2) was added to individual wells and further incubated at 4° C. overnight, to achieve equilibrium. Any unbound ANG was removed by repeated washing with PBS-Tween. Interactions between ANG and LF were measured by using avidin-conjugated alkaline phosphatase reagent, followed by a color reaction with the addition of p-nitrophenyl phosphate (PNP), a chromatophore substrate. The rate of color development was measured at 405 nm, in a kinetic manner for 30 min. The rate of enzymatic hydrolysis of PNP chromatophore as function of concentration of biotin-ANG was plotted to measure the binding interactions.

FIG. 2 depicts the interactions of biotinylated LF with (fdn)-ANG (subset-A), and biotinylated ANG with (fdn)-LF (subset-B), respectively, as measured by kinetic ELISA. The rate of PNP substrate hydrolysis by avidin-alkaline phosphatase, as measured by kinetic ELISA, indicated the interaction of biotinylated protein(s) with (fdn)-ANG or -LF. Data shows the formation of ANG-LF complexes in a dose-dependant manner.

Example-4

Preparation of ANGex Using Lipid-Based Substrates

Based on its cationic properties, ANG is incorporated into the anionic lipid films and matrices by electrostatic interactions. A fatty acid-like stearic acid (Octadecanoic acid C18H36O2) is thermally coated under vacuum on a quartz cover slip or quartz crystal resonator of the type used in Quartz Crystal Microbalance (QCM) technique. This process is known to produce a film of few hundred angstrom thickness. The stearate-coated quartz cover slip is immersed in 0.1% ANG solution (in 50 mM sodium phosphate buffer) at 4° C. for 30 min. The quartz cover slip is removed from the ANG solution, washed thoroughly in deionized water and dried under gentle flow of dry nitrogen gas.

Measurement of ANG Interaction with Lipid Film by QCM

Immobilization of ANG on a thermal evaporated fatty acid film was monitored by measuring changes in the frequency of quartz crystals using QCM instrument (Edwards FTM5 microbalance) at 1 Hz resolution. The frequency changes are converted to mass loading using the Sauerbrey equation. The quartz cover slip is also used for recording the UV absorption spectrum of the film before and after the lipid immobilization of ANG. The difference in the UV spectrum indicated the immobilization of ANG on the lipid film (Sauerbrey G., *Z. Phys.* 155:206, 1959; Buttry D A, et al., *Chem. Rev.* 92:1356-1379, 1992; Sastry M., *Trends in Biotechnology* 20:185-188, 2002).

ANG was immobilized and entrapped in the lipid matrix primarily by electrostatic interactions. The use of charge interactions also enabled "leaching-out" of the entrapped ANG when immersed in solution at pH 2.0. Soft lipid matrix enabled the entrapment without significant distortion of the tertiary structure of the ANG, therefore, the bio-functional properties of the protein molecule is well preserved.

Example-5

Preparation of ANGex Using Coenzyme/Vitamin-Based Substrates

Coenzyme-Q10 (CoQ-10), due to its quinone structure, is extremely lipophilic, soluble in ethanol and chloroform, but practically insoluble in water. A detergent like sodium glycocholate along with sonication generates a submicron-sized dispersion of CoQ-10 in phospholipid (from soy bean). The detergent also inhibits re-crystallization of CoQ-10. This dispersion has been used in the preparation of micro-emulsions to incorporate ANG (Stojkovic M, et al., *Biol. Reprod.* 61:541-547, 1999).

Phospholipid Lipoid S 100 (Lipoid KG, Germany) is a mixture of phosphatidylcholine from fat-free soybean lecithin that consists mainly of linoleic phosphatidylcholine. S 100 was melted together with CoQ-10 (Alchem, India) at 65° C. Sodium glycocholate (NaGC) was dissolved in distilled water containing 2.25% (w/w) glycerol. This mixture was heated to 65° C. and mixed with the molten lipid phase. The hot mixture was sonicated for 30 min. while maintaining a constant temperature. This hot emulsion was sterile-filtered (0.22 μm) into vials and allowed to cool at room temperature. Stabilizer dispersion without CoQ-10 was also prepared in a similar manner. Calculated amounts of the two dispersions were mixed to prepare dispersions containing various concentrations of CoQ-10.

ANG stock solution was freshly prepared using 50 mM phosphate buffer, pH 8.0, containing 0.2% sodium cholate. This solution was diluted with 50 mM phosphate buffer, pH 7.4, containing 0.2% sodium cholate to a protein concentration of 1 mg/mL. The ANG-CoQ-10 complexes were prepared by mixing 500 μL aliquots of diluted ANG solution with 500 μL of ubiquinone dispersions at various concentrations up to 100 μM. The mixtures were kept in an incubator-shaker at 25 C for 1 h, before characterization by antioxidant assay.

ANG-NADH complex was prepared by mixing 500 μL of ANG (1 mg/mL) solution with 500 μL of β-NADH-dipotassium salt (0.1 mg/mL) solution in 50 mM phosphate buffer, pH 7.4.

Ascorbic acid has pKa value of 4.2 and would complex with ANG. This complex was prepared by mixing 500 μL of ANG (1 mg/mL) solution with 500 μL of ascorbate solutions of different concentrations in 50 mM phosphate buffer, pH 7.4.

Vitamins A and E are also fat-soluble and their complex with ANG was also prepared by dispersion in soy phospholipids, as described with CoQ-10 complexes Example-6

Preparation of ANGex Using Nucleic Acid/Nucleotide-Based Substrates

DNA, RNA and nucleotides are negatively charged due to the presence of phosphate groups. These molecules form complexes via the positively charged residues on basic proteins such as ANG. The characterization of the affinity and shape of the ANG-nucleotide complex is performed using Gel Mobility Shift assay (Bading H. *Nucleic Acids Research* 16:5241-5248, 1988). The DNA-binding assay using mobility-shift polyacrylamide gel electrophoresis (PAGE) is based on the observation that protein/DNA complexes migrate through polyacrylamide gels more slowly than unbound DNA fragments.

ATP-protein complex was formed by the treatment of the ANG with ATP (Sigma). ATP (10 μmoles) was incubated with ANG (5 mg) and 40 μM Tris-acetate buffer, pH 7.0, in a total volume of 1 mL for 10 min at room temperature. The complex was centrifuged, washed, and the ATP:Protein ratio determined (Richardson S H, et al., Proc. Natl. Acad. Sci. USA 50:821-827, 1963).

Example-7

Preparation of [ANGex]+[(Fdn)-ANG] Mixtures

The molecular ratio of ANGex versus (fdn)-ANG is important for the specificity, multi-functionality and molecular stability of both the immobilized and the native ANG proteins. Mixtures of ANGex and (fdn)-ANG are formed by adding excess (fdn)-ANG during the immobilization, conjugation or complexation process. Mixtures of ANGex and (fdn)-ANG in a ratio of from about 100:1 to about 1:100, preferably from about 10:1 to about 1:10, most preferably 1:1 ratio have been found to provide the optimum stability and functionality.

Example-8

Detection of ANGex

The formation of ANGex was confirmed by a turbidity titration method, commonly used to study formation of several macromolecular complexes such as protein-DNA and protein-polyelectrolyte complexes. During formation of ANGex (i.e. ANG+LF complex), the interaction is accompanied by an increase in the macromolecular size that results in the increase of incident light scattering. The relative light scattering is quantified by spectral analysis as apparent absorbance at 600 nm, while subtracting any interfering absorbance from the sample or buffer (Zhou Y, et al., *Biophys Chem* 107:273-281, 2004; Xia J, et al., *Langmuir* 9:2015-2019, 1993).

FIG. 3 shows the detection and measurement of ANGex by turbidity titration method. The assay is based on measurement of $A_{600}$ for a series of LF solutions to which increasing amounts of ANG was added. ANGex (ANG+LF complex) was prepared in a series of samples with varying amounts of ANG (0 to 25 μM) with LF (5 μM) solution in 20 mM phosphate buffer. The protein absorbance at 280 nm showed a linear increase with the molar ratio [ANG]/[LF] of the complex forming proteins. The relative light scattering as measured by the absorbance at 600 nm, plotted against the molar concentration ratio of ANG to LF indicated non-linear increase in macromolecular size due to ANGex complex formation. (Inset) shows linear increase in $A_{280}$ absorbance for the above series of solutions.

Isolation of ANGex

ANGex with carbohydrate or protein substrates are isolated by size-exclusion and/or ion-exchange chromatography. Due to larger size, ANGex is eluted earlier than the free proteins or free carbohydrates on the size-exclusion column. A size-exclusion column (TSKgel G4000PW, Tosoh Biosep, Japan) was equilibrated with 20 mM sodium phosphate buffer, pH 7.2. The ANGex solution was injected into to the column and subsequently eluted with sodium phosphate buffer at a flow rate of 0.5 mL/min.

During isolation with cation exchange column (UNO-S; Bio-Rad), a solution containing ANGex was applied to a cation exchange column which was equilibrated with 20 mM sodium phosphate buffer (pH 7.2). A flow rate for the buffer was continued at 1 mL/min for 30 min to ensure removal of unbound chemical residues from the ANGex solution. The bound ANGex was eluted by flow of salt gradient (1 M NaCl in phosphate buffer). In the case of ANG-LF complex, free proteins and the complex were eluted as separate peaks at distinct salt concentrations. However, for ANG-GAG complex, a combination of a cation-exchange and an anion exchange columns were used in series, since such complex shows residual negative charge from the GAG component and binds to anion-exchange column along with free GAG. On the other hand, the free protein due to its positive charge binds to the cation-exchange column. The bound complexes are eluted using a salt gradient flow separately from respective columns.

FIG. 4 shows the separation of ANGex from free LF, on UNO-S cation-exchange chromatogram using NaCl gradient (60-80% B in 80 min). Unbound (fdn)-LF (50 μM) eluted as a single peak at retention time of 123.3 min (Curve 1). The retention time of (fdn)-LF peak decreased to 121.6 min for ANGex with ANG/LF molar ratio 1.0 (Curve 2). Elution of ANGex was monitored by measuring absorbance at 214 nm.

Example-9

Molecular Stability of ANGex

The three-dimensional structure of ANG at the physiological pH and temperature conditions is responsible for it multi-functional activity. Changes in milieu conditions such as the pH, ionic strength, as well as interaction of ANG with other proteins, ligands and denaturants influence the structure-functional properties of the native state. Higher temperatures also lead to unfolding of the native structure leading to diminished or total loss of ANG activity. Data on changes in the secondary structure of ANG were obtained using Circular Dichroism (CD) spectrophotometric assay. ANG polypeptide backbone is optically active in the far ultraviolet region (170-250 nm) and different secondary structures exhibit characteristic CD spectra.

In an experiment to study the acid-tolerance/resistance of ANGex, a series of samples were prepared with 10 μM of ANGex, dissolved in 1-mL of buffers with varying pH ranging from 2.0 to 8.0. After incubation at 37° C. for 30 min with gentle shaking, the CD spectrum of each of the sample was recorded using a CD spectrophotometer (Jasco, Japan). Comparison of the CD spectra of ANGex samples in the range 190-240 nm, with that for ANGex at pH 7.2 revealed only minor changes in the secondary structure of the complex. This observation confirmed that ANGex is stable to changes in pH of the solution.

A similar experiment was carried out in order to assess the thermo-stability of ANGex. A series of ANGex samples (10 μM) in 50 mM acetate buffer, pH 5.5, were incubated at different temperatures (50, 60 and 70° C.) for various time points (5, 10, 30, and 60 min). After incubation, the CD spectrum of each of the sample was recorded using a CD spectrophotometer equipped with a thermostatic cell holder.

There were no significant changes in the CD profile of ANGex at higher temperatures when compared with the profile at room temperature, confirming that ANGex remained its native structure at elevated temperatures.

Measurement of ANG Activity by Placental RNase Inhibitor (PRI) Assay

For both acid and thermal stability testing protocols, the residual activity of ANGex was monitored by an in vitro binding assay for ANG using PRI (Bond M D., *Anal. Biochem.* 173:166-173, 1988). In brief, test samples (volume range: 0 to 40 μL) were added to 40 μL 0.5 M Tris buffer, pH 7.5 (with 5 mM EDTA, 10 mM DTT, 0.5 mg/mL human serum albumin) containing of 0.53 pmol PRI (Sigma). The mixtures were made up to a final volume of 90 μL with deionized RNase-free water, incubated for 5 min for optimal interaction between ANG and PRI, followed by an addition of RNase A (0.58 pmol of RNase A in 10 μL of 5 mM Tris, 0.1 mg/mL lysozyme, pH 7.5). The reaction was initiated by the addition of 0.1-mL of 1% yeast RNA (freshly dissolved in RNase-free water and passed through a sterile 0.45 μm filter). After incubation for 25 min at 25° C., the reactions were terminated with 0.2-mL ice-cold quenching reagent (1.16 N perchloric acid with 5.9 mM uranyl acetate) and the mixture was homogenized and placed on ice for 25 min. After centrifugation at 4° C. (15000×g for 5 min.), test samples were made from 0.2-mL aliquots diluted to 1-mL volume with 5 mM Tris, pH 7.5 containing 0.1 mg/mL lysozyme (in order to minimize adsorption to container surfaces). The absorbance at 260 nm was recorded for each sample and subtracted from that of a blank solution prepared in an identical manner except that water was added instead of RNase, to give $\Delta A_{260}$.

A linear relationship between the RNase concentration and increased absorption at 260 nm due to the presence of the acid-soluble nucleotides produced from the hydrolysis of the yeast RNA, is observed. Two types of standards were used with each binding assay, i) containing 0.58 pmol (2.9 nM) RNase A in the absence of PRI or ANG ($\Delta AE$); and ii) containing both the RNase A and 0.53 pmol (2.6 nM) PRI ($\Delta AEI$). These standards represent the maximum and minimum obtainable $\Delta A_{260}$ values, respectively, in the absence of ANG in the sample. Increases in $\Delta A_{260}$ values above the minimum are proportional to the amount of ANG present, and the concentration is calculated using the equation: $[ANG] = [(\Delta Asample - \Delta AEI)/\Delta AE] \times 2.9$ nM. Wherein, $\Delta Asample$, $\Delta AEI$ and $\Delta AE$ are absorbance values of the sample, the RNase A plus PRI standard assay, and the RNase A standard, respectively. In particular cases, when impure samples are assayed, concentrations are expressed in terms of RNase A equivalents in μg/mL instead of nanomolar ANG concentration. A comparative activity of ANG, before and after incubation at different temperatures as well as incubation in buffers at various pH, are used in the estimation of acid-tolerance/resistance and thermo-stability of ANGex and ANG samples.

Example-10

Measurement of Functional Activities of ANGex

RNase Activity of ANGex

RNase activity of ANG is far lower than that of RNase A (Ribonuclease A) and therefore a highly sensitive assay was used to measure this enzymatic activity. This assay monitors the kinetics of cleavage of fluorescent tagged oligonucleotides (substrates) by ANGex and measures the fluorescence emission following the cleavage (Park C et al., Biochemistry 41:1343-1350, 2002).

The RNase substrates are short oligonucleotides of sequences (AUAA, AAUAAA, AAAUAAAA) each attached to a fluorophor, 6-carboxy fluorescein (6-FAM) at the 5' end and to a quencher, 6-carboxytetramethyl-rhodamine (6-TAMRA) at the 3' end. When the substrate is intact, 6-TAMRA quenches the fluorescence of 6-FAM. Ribonucleolytic cleavage of the substrate results in the fluorescence emission by 6-FAM. RNase substrate (6 nM) solution was prepared in 1 mM Bis-Tris buffer, pH 6.0 containing 0.1M NaCl. A 2-mL substrate solution was mixed with 50 nM ANGex and tested at 25° C. Fluorescence emission of the reaction mixture was measured at 515 nm with excitation at 490 nm using a fluorescence spectrophotometer (QuantaMaster 1, Photon Technology International, NJ). Values of $\Delta F/\Delta t$ were determined by a linear least squares regression analysis of the initial fluorescence (F) with time (t). This rate was further used in the following equation: $kcat/KM = \{(\Delta F/\Delta t)/(Fmax - F0)\} \cdot (1/[E])$, where [E] is the concentration of ANGex. Fmax is obtained from a separate experiment by adding 0.1 μM RNase A to the reaction mixture and F0 is the initial fluorescence intensity without ANG.

A comparison of the kcat/KM for (fdn)-ANG with that of ANGex prepared from different substrates indicated the effect of immobilization.

Antimicrobial Activity of ANGex

Microbial metabolism cause electrical charge alterations in cultivation media due to breakdown of nutrients. A Bactometer® Microbial Monitoring System Model-128 (bioMerieux Vitek, Hazelwood, Mo.) was used to monitor bacterial growth by measuring impedance signals (a function of both capacitance and conductance) in the cultivation media. Growth Impedance Detection Assay (GIDA). Growth Impedance Detection Assay (GIDA) was performed in 16-well modules; briefly, a volume of 0.5-mL double-strength tryptic soy broth (2×TSB) was added to each well. A volume of 0.25-mL of test sample (final concentration: 1 mg/mL) followed by 0.25-mL of bacterial suspension (104 cells/mL) prepared in 0.9% saline was added to the wells. Addition of 0.5-mL saline or bacterial suspension to module wells with 0.5-mL TSB (2×) served as controls for sterility and growth, respectively. The inoculated modules (final volume: 1-mL) were incubated at 37° C., and impedance changes in the media was continuously monitored by the Bactometer® at 6-min intervals for 48-h. Bacterial growth curves were graphically displayed as percent changes of impedance signals versus incubation time. The amount of time required to cause a series of significant deviation from baseline impedance value was defined as the 'detection time' (DT). Difference in DT values between growth control and test samples was considered as the 'stasis' (growth-inhibition) time.

The antimicrobial activity of ANGex (immobilized on GRP) was compared with that of (fdn)-ANG and GRP (galactose-rich polysaccharide from agar) activities, tested at 1 mg/mL concentration. ANG demonstrated ability to inhibit the growth of various microbial pathogens. The immobilization process of the free dispersed native ANG with GRP substrate resulted in the generation of an ANGex complex with enhanced microbial growth inhibition activity as shown in Table-1.

TABLE 1

Antimicrobial activity of ANG and ANGex (immobilized on GRP)

| | IMPEDENCE DETECTION TIME (Stasis) | | |
|---|---|---|---|
| TEST STRAIN | Control (h) | ANG | ANGex |
| *Escherichia coli* ATCC433895 | 5.1 | 9.0 (3.9-h) | 11.4 (6-3-h) |
| *Salmonella typhimurium* ATCC14028 | 6.2 | 8.6 (2.4-h) | 10.5 (4.3-h) |
| *Pseudomonas aeruginosa* ATCC27853 | 12.5 | 28.7 (16.2-h) | 36.0 (23.5-h) |
| *Klebsiella pneumoniae* ATCC13883 | 7.2 | 11.4 (4.2-h) | 14.5 (7.3-h) |

TABLE 1-continued

Antimicrobial activity of ANG and ANGex (immobilized on GRP)

| TEST STRAIN | IMPEDENCE DETECTION TIME (Stasis) | | |
|---|---|---|---|
| | Control (h) | ANG | ANGex |
| Staphylococcus aureus ATCC25923 | 11.8 | 16.6 (4.8-h) | 21.4 (9.6-h) |
| Staphylococcus epidermidis ATCC12228 | 14.5 | 27.6 (13.1-h) | 28.0 (13.5-h) |
| Streptococcus pyogenes ATCC19615 | 15.2 | 32.9 (17.7-h) | 40.0 (24.8-h) |
| Candida albicans | 8.1 | >48.0 (>40-h) | >48.0 (>40-h) |

Antioxidant Activity of ANGex

Ferric reducing/antioxidant power (FRAP) assay (Benzie I F, et al., Methods in Enzymology: Oxidants and Antioxidants, ed. L Packer, pp 15-27, Orlando: Academic Press, 1999) with minor modifications has been used to measure the antioxidant activity of ANGex complexes. The FRAP reagent was prepared by mixing 40 mL of 0.3 M acetate buffer (pH 3.6), 4 mL of 20 mM ferric chloride, and 4 mL of 10 mM TPTZ [2,4,6-Tris(2-pyridyl)-s-triazine]. Serial dilutions (0.1 to 1.0 mM) of 6-OH-2,5,7,8-tetramethyl chroman-2-carboxylic acid (CAS 53188-07-1) were used as FRAP standards. All reagents were brought to 37° C. prior to the assay. FRAP assay was performed in a 96-well microplate by mixing 20 µL of DI water, 10 µL of ANGex complex sample, and 150 µL of FRAP reagent. In combination studies 10 µL of DI water and 20 µl of ANGex were mixed with 150 µL of FRAP reagent. After instant incubation at 37° C. for 5 min (for ascorbic acid) and for a time lapse of 5 min to 24 h (for ANGex and milk-derived ANG) the absorbance of reaction mixtures was measured at 593 nm (Spectramax 340PC).

The FRAP reaction kinetics (measured as the rate of increase in absorbance of reaction mixtures at 593 nm) of ANGex was compared with its source material, the (fdn)-ANG from bovine milk, (fdn)-LF from bovine milk and antioxidant standards (i.e. vitamin-C, TROLOX and FeSO4).

FIGS. 5 A & B shows the antioxidant activity of ANGex as determined by kinetic FRAP assay by measuring the increase in absorbance at 593 nm. The antioxidant efficiency (r) was measured as change in absorbance with the concentration of ANGex formed at different compositions. In FIG. 5A, the FRAP activity of ANGex formed by the interaction of 694 µM of (fdn)-ANG with 125 µM of (fdn)-LF, is compared with the corresponding individual activities of the same concentration of (fdn)-LF and (fdn)-ANG, under the same test conditions. All the systems studied show activity in three stages, with a gradual rise in the initial 14 hours, a steep rise in the period 14-18 hours and saturation in the final 6 of twenty four hours. ANGex showed consistently higher absorbance throughout the duration of the experiment. After the initial 14-h, ANGex had an absorbance of 0.47, while (fdn)-forms of ANG and LF were at 0.29 and 0.14, respectively. After 24-h, the maximum absorbance at 593 nm, attained by (fdn)-LF and (fdn)-ANG are 0.87 and 0.64, respectively, whereas ANGex demonstrated a maximum absorbance of 1.18, which is a 35% increase from that of (fdn)-LF and a 84% increase from that of (fdn)-ANG. FIG. 5B shows that when individually tested, (fdn)-ANG demonstrated antioxidant efficiency (r) of 0.65 Abs/mM. When complexed with 25 µM of LF, the 'r' value increased to 0.67, indicating an enhancement of the antioxidant power. At the same, ANG complexed with higher concentrations, 75 and 125 µM of LF showed significantly reduced 'r' values of 0.3 and 0.38, respectively.

DEFINITION OF TERMS

Angiogenic activity is the chemical stimulation of hemovascular development in tissue. It is generally associated with diffusible substances produced by a variety of cell types.

Angiogenin: As used herein, "angiogenin" or "ANG" refers to an angiogenic-stimulating factor, which is also 14-kDa heparin-binding protein that occurs in most cells, also present in various biological fluids such as plasma and milk.

ANGex: Refers to immobilized or conjugated angiogenin complexes with naturally occurring substrates.

Angiogenic stimulators: As used herein, "angiogenic stimulators" refers to growth factors that stimulate neogenesis and regeneration of vascular tissue including the cardiac muscles. These growth factors include, but not limited to, angiogenin, vascular endothelial growth factor (VEGF), fibroblast growth factor-acidic (FGF-a), fibroblast growth factor-basic (FGF-b), tumor necrosis factor (TNF)-a, and transforming growth factor (TGF)-$\alpha/\beta$.

Angiogenic inhibitors: As used herein, "angiogenic inhibitors" refers to physiological regulators that inhibit biosynthesis of vascularization process. These regulatory compounds include, but not limited to angiostatin, thrombospondin-1 and interferon-$\alpha/\beta$, platelet factor factor-4, 16 kDa N-terminal fragments of prolactin, and endostatin.

Galactose-rich polysaccharide (GRP): Suitable galactose-rich polysaccharides include galactose derivatives comprising galactose, anhydrogalactose, 2-O-methyl-galactose, and 4-O-methyl-galactose, among others. The GRP substrates can be purchased or extracted from commercial agars by known methods. Acid hydrolysis of agar under mild conditions leads to cleavage of glycosidic bonds between C-1 of 3,6-anhydro-L-galactose and O-3 of D-galactose residues that exposes D-galactosyl residues and leads to the formation of galactose-rich polysaccharides (GRP) (Gray G. Arch. Biochem. Biophys. 163:426-428, 1974; Lee R T, et al., Biochemistry 19:156-163, 1980).

Lactoferrin (LF): As used herein, "lactoferrin", or "LF" refers to various protein preparations and forms, including but not limited to, lactoferrin-(tcr) (as described in Naidu U.S. Pat. No. 7,125,983), freely-dispersed native (fdn)-lactoferrin which includes metal-saturated (holo), partially saturated and metal-free (apo) forms of LF. The LF-bound metal is preferably copper, and other bound metals include zinc, iron, manganese, chromium, aluminum and gallium. The term LF further refers to fully and partially glycosylated polypeptide chains of LF, incomplete polypeptide chains including half-molecules comprising C- and N-terminus lobes of LF. The term LF categorically excludes aggregated-LF and immobilized (Im)-LF forms (as described in Naidu U.S. Pat. No. 6,172,040 B1, issued Jan. 9, 2001) that are devoid of any (fdn)-LF.

Mitogenic activity is the chemical stimulation of cell division.

Ribonuclease (RNAse) activity is characterized by the degradation of large RNA molecules, such as the 28S and 18S ribosomal RNAs, to lower molecular weight species.

Freely-dispersed native (fdn): As used herein, "freely-dispersed native" (fdn) refers to isolated protein molecules free of auto-aggregation or polymerization and free from binding or immobilization to other substrates.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An antimicrobial composition comprising osteopontin, an isolated angiogenin non-covalently complexed to lactoferrin and at least one antimicrobial protein selected from the group consisting of myeloperoxidase (MPO), salivary peroxidase (SPO) and lysozyme.

2. The antimicrobial composition of claim 1, wherein the angiogenin is isolated from a biological fluid.

3. The antimicrobial composition of claim 2, wherein the biological fluid is selected from the group consisting of colostrum, milk, whey, milk serum, blood, plasma and serum.

4. The antimicrobial composition of claim 2, wherein the biological fluid is obtained from a mammal and wherein the mammal is selected from the group consisting of cows, buffalos, horses, sheep, pigs and camels.

5. The antimicrobial composition of claim 4, wherein the mammal is genetically modified.

6. The antimicrobial composition of claim 1, further comprising native angiogenin.

7. The antimicrobial composition of claim 6, wherein the composition comprises complexed angiogenin and native angiogenin at a ratio of 1:1 to 1:10.

8. The antimicrobial composition of claim 6, which further comprises a buffer system, a physiological acceptable base and a salt.

9. The antimicrobial composition of claim 8, wherein the buffer system is selected from the group consisting of oxalic acid, ethylenediamine tetraacetic acid and citric acid.

10. The antimicrobial composition of claim 8, wherein the physiological acceptable base is sodium bicarbonate.

11. The antimicrobial composition of claim 8, wherein the salt is selected from the group consisting of sodium chloride, potassium chloride and calcium chloride.

12. A method of inhibiting microbial growth comprising administering the composition of claim 1 to a subject in need thereof.

13. The method of claim 12, wherein the microbe is selected from the group consisting of *Escherichia coli, Salmonella typhimurium, Pseudomonas aeruginosa, Klebsiella pneumonia, Staphylococcus aureus, Staphylococcus epidermidis, Streptococcus pyogenes,* and *Candida albicans.*

* * * * *